US012733936B2

(12) United States Patent
Büchert et al.

(10) Patent No.: US 12,733,936 B2
(45) Date of Patent: Sep. 15, 2026

(54) MEDICAL KIT, MEDICAL SYSTEM, AND COVERING DEVICE FOR THE TREATMENT OF ANEURYSMS

(71) Applicant: Acandis GmbH, Pforzheim (DE)

(72) Inventors: Michael Büchert, Pforzheim (DE); Giorgio Cattaneo, Karlsruhe (DE)

(73) Assignee: Acandis GmbH, Pforzheim (DE)

( * ) Notice: Subject to any disclaimer, the term of this patent is extended or adjusted under 35 U.S.C. 154(b) by 944 days.

(21) Appl. No.: 17/786,661

(22) PCT Filed: Dec. 17, 2020

(86) PCT No.: PCT/EP2020/086616
§ 371 (c)(1),
(2) Date: Jun. 17, 2022

(87) PCT Pub. No.: WO2021/122877
PCT Pub. Date: Jun. 24, 2021

(65) Prior Publication Data

US 2023/0044123 A1 Feb. 9, 2023

(30) Foreign Application Priority Data

Dec. 20, 2019 (DE) ..................... 10 2019 135 502.8

(51) Int. Cl.
*A61F 2/82* (2013.01)
*A61B 17/12* (2006.01)
(Continued)

(52) U.S. Cl.
CPC .... *A61B 17/12118* (2013.01); *A61B 17/1214* (2013.01); *A61F 2/07* (2013.01);
(Continued)

(58) Field of Classification Search
CPC ...... A61B 17/12118; A61B 2017/3419; A61B 17/12113; A61F 2/90; A61F 2/07; A61F 2250/0098
(Continued)

(56) References Cited

U.S. PATENT DOCUMENTS 5,769,884 A 6/1998 Solovay
6,685,669 B2 2/2004 Bellhouse et al.
(Continued)

FOREIGN PATENT DOCUMENTS

DE 102019121546 A1 8/2019
EP 2964161 B1 5/2019
(Continued)

OTHER PUBLICATIONS

Translation of WO 2014/071837 (Year: 2014).*
(Continued)

*Primary Examiner* — Brian E Pellegrino
(74) *Attorney, Agent, or Firm* — Cesari and McKenna, LLP

(57) ABSTRACT

The disclosure relates to a medical kit for the treatment of vascular malformations, in particular aneurysms and/or fistulas, having a permanently implantable covering device, in particular a stent, for covering the vascular malformation, the covering device having a tubular, self-expandable lattice structure and a covering made of an electrospun fabric, the covering being connected to the lattice structure and overlapping the lattice structure at least in part such that, when implanted, the covering is placed over the vascular malformation; and an embolisation means, which can be applied by a feed means in the implanted state for treatment of the vascular malformation, the covering forming a porous membrane which can be penetrated by the feed means for application of the embolisation means and which is designed
(Continued)

to lie against the outer periphery of the feed means in the penetrated state.

18 Claims, 9 Drawing Sheets

(51) Int. Cl.
*A61F 2/07* (2013.01)
*A61F 2/90* (2013.01)

(52) U.S. Cl.
CPC .......... *A61F 2/90* (2013.01); *A61F 2002/072* (2013.01); *A61F 2002/823* (2013.01)

(58) Field of Classification Search
USPC .......................................................... 606/200
See application file for complete search history.

(56) References Cited

U.S. PATENT DOCUMENTS

| | | | | |
|---|---|---|---|---|
| 9,005,695 | B2 | 4/2015 | Shank et al. | |
| 2004/0054406 | A1 | 3/2004 | Dubson et al. | |
| 2006/0085063 | A1 | 4/2006 | Shastri et al. | |
| 2009/0054966 | A1 | 2/2009 | Rudakov et al. | |
| 2009/0069880 | A1 | 3/2009 | Vonderwalde et al. | |
| 2009/0264990 | A1* | 10/2009 | Bruszewski | A61F 2/07 623/1.13 |
| 2013/0018452 | A1* | 1/2013 | Weitzner | A61F 2/90 623/1.15 |
| 2014/0058498 | A1 | 2/2014 | Hannes et al. | |
| 2018/0207009 | A1* | 7/2018 | Nordhausen | A61F 2/07 623/1.13 |
| 2018/0338847 | A1 | 11/2018 | Holzer et al. | |
| 2019/0298390 | A1 | 10/2019 | Yamanouchi et al. | |

FOREIGN PATENT DOCUMENTS

| | | | | |
|---|---|---|---|---|
| WO | WO-2009019664 | A2 * | 2/2009 | A61F 2/07 |
| WO | WO-2009089055 | A1 * | 7/2009 | A61F 2/91 |
| WO | WO-2014/007631 | A1 | 1/2014 | |
| WO | WO-2014071837 | A1 * | 5/2014 | A61F 2/90 |
| WO | WO-2014177634 | A1 | 11/2014 | |
| WO | WO-2019175341 | A1 | 9/2019 | |

OTHER PUBLICATIONS

German Office Action, dated Oct. 12, 2020, German Patent Application No. DE 10 2019 135 502.8, 6 pages.

PCT Notification of Transmittal of the International Search Report and the Written Opinion of the International Searching Authority, or the Declaration, International Searching Authority, International Application No. PCT/EP2020/086616, mailed Apr. 16, 2021, 14 pages.

* cited by examiner

MEDICAL KIT, MEDICAL SYSTEM, AND COVERING DEVICE FOR THE TREATMENT OF ANEURYSMS

CROSS REFERENCE TO RELATED APPLICATIONS

The present application is a National Stage of International Application No PCT/BP2020/086616, filed Dec. 17, 2020, which application claims priority to commonly owned German Patent Application No. 102019135502.8, filed on Dec. 20, 2019, which applications are incorporated herein by reference in their entirety.

TECHNICAL FIELD

The invention relates to a medical set for the treatment of vascular malformations, in particular aneurysms and/or fistulas. Furthermore, the invention relates to a medical system as well as to a covering device for the treatment of vascular malformations.

BACKGROUND

WO 2014/177634 A1 describes a highly flexible stent which has a compressible and expandable mesh structure, wherein the mesh structure is formed in one piece. The mesh structure comprises closed cells which are each delimited by four mesh elements. The mesh structure has at least one cell ring which comprises between three and six cells.

Furthermore, in the Applicant's experience, stents with mesh structures are known which are formed from a single wire. The wire is braided with itself in order to form a tubular network. At the axial ends of the tubular network, the wire is curved round so that loops which act atraumatically are formed. The axial ends may flare outwards in a funnel shape.

The known medical device is particularly suitable for the treatment of aneurysms in small cerebral blood vessels. Blood vessels of this type have a very small cross sectional diameter and are often highly tortuous. For this reason, the known stent is highly flexible in configuration, so that on the one hand it can be compressed to a very small cross sectional diameter, and on the other hand it has a high bending flexibility, which enables it to be delivered to small cerebral blood vessels.

For the treatment of aneurysms in cerebral blood vessels, it is advantageous to use stents which bridge an aneurysm and screen it from the flow of blood inside the blood vessel. To enable this, providing stents with a covering is known; it occludes the cells of the stent and thus prevents the flow of blood into an aneurysm.

A further supplementary or alternative method for the treatment of aneurysms is the implantation of what are known as coils into the aneurysm which, once there, lead to the production of a blood clot. The resulting thrombus then prevents blood from circulating in the aneurysm and thus removes the risk of a rupture with associated haemorrhage.

In particular in the case of broad-neck aneurysms, however, the coils have a tendency to displace during implantation into the blood vessel and thus cause the main vessel lumen to become occluded. In the "Balloon Assisted Coiling" technique, catheters are positioned in the vessel with "Compliance Balloons", in particular at the level of the neck of the aneurysm. The balloon, which is filled with contrast agent, then occludes the neck of the aneurysm during placement of the coil and forces the coil into a compact arrangement inside the aneurysm sac. Because coils are plastically deformable, they then remain in their shape. In addition, they do not come out of the aneurysm when the balloon is removed. However, a problem arises in this regard, in particular because of the fact that the balloon occludes the vessel. In a lengthy procedure (in the case of large aneurysms, several coils are positioned, and the procedure can last several minutes), the flow of blood is completely cut off during that time. Even though collateral vessels supply downstream tissue, the risk of underperfusion still remains.

Furthermore, during the procedure, a catheter through which the coils are fed becomes "jailed", i.e. wedged at the side of the balloon. In the event that the coil catheter has to be changed (for example in the case of damage) when the procedure has not yet been completed, the balloon has to be deflated (emptied) in order to be able to withdraw the catheter. In this phase, coils which are not yet fully compacted in the vessel could become displaced. This could then result in occlusion of the vessel.

SUMMARY

In the light of the foregoing, the objective of the invention is to provide a medical set for the treatment of vascular malformations with the aid of which the risk of occlusion of a vessel is at least reduced. A further objective of the invention is to provide a medical system.

In accordance with the invention, this objective is achieved in respect of the medical set by the subject matter of the patent claims.

Specifically, the objective is achieved by means of a medical set for the treatment of vascular malformations, in particular aneurysms and/or fistulas, for example a carotid direct cavernous fistula. The set has a permanently implantable covering device, in particular a stent, for covering the vascular malformation. The covering device has a tubular self-expandable mesh structure and a covering produced from an electrospun fabric. The covering is connected to the mesh structure and at least partially covers the mesh structure in order to be placed over the vascular malformation in the implanted state. The medical set has an embolisation means which, in the implanted state, can be applied by means of a delivery means for the treatment of the vascular malformation. The covering forms a porous membrane which can be penetrated by the delivery means for the application of the embolisation means and to this end is adapted to lie against the outer circumference of the delivery means when in the penetrated state.

The medical set in accordance with the invention therefore comprises the covering device and the embolisation means. The set may comprise other components.

In contrast to the medical set in accordance with DE 10 2019 121 546 of 9 Aug. 2019, the medical set in accordance with the invention is intended to cover an aneurysm permanently and not simply temporarily. The covering device forms a permanent implant such as a stent, for example. In this regard, the permanently implantable covering device is placed over the aneurysm to be treated with the aid of a transport wire via the delivery means in a known manner. After the covering device has been completely discharged from the delivery means, it is released from the transport wire. In this manner, the covering device is securely and permanently anchored in the vessel and in the final implanted state, it can no longer be drawn into the delivery means.

In this regard, the covering device is releasably connected to the transport wire during introduction.

The covering device is preferably a stent. In general, the covering device has a tubular and self-expandable mesh structure. The mesh structure is open at the distal and proximal ends, i.e. open at both axial ends, so that when in the expanded state, blood can flow through it in known manner. In contrast to this, for the purposes of withdrawing back into a catheter, known thromboectomy devices have an inwardly occluding funnel-shaped section which is securely connected, i.e. not releasably connected, to the transport wire.

The covering formed by the electrospun fabric on the mesh structure has an extent such that in the implanted state, a vascular malformation, in particular an aneurysm, can be sufficiently securely covered. In this regard, the covering may extend over the entire circumference of the mesh structure and over a sufficiently long length in the axial direction of the mesh structure. It is also possible for the covering to extend over only part of the circumference of the mesh structure, in particular over an angular segment of the mesh structure, rather than over the entire circumference, and/or over part of the length.

The covering is connected to the mesh structure in a manner such that in the implanted state, it cannot be released from the mesh structure. The electrospun fabric of the covering covers the mesh structure.

In general, the embolisation means are those which are suitable for the treatment of vascular malformations. Non-exclusive examples of embolisation means which are introduced into the aneurysm for the purposes of atrophying are a coil or a plurality of coils and/or liquid embolics such as viscous hydrogels.

In accordance with the invention, the covering, specifically the electrospun fabric of the covering, forms a porous membrane. In this regard, the entire covering, specifically the electrospun fabric of the covering, may form the porous membrane. It is also possible for only a portion of the covering to form the porous membrane.

The porous membrane is configured in a manner such that it can be penetrated by the delivery means in order to apply the embolisation means. In other words, the porous membrane is configured in a manner such that the delivery means can be perforated from the inner lumen of the implanted mesh structure radially outwards or at an acute angle outwards through the membrane. In this regard, the delivery means pierces or penetrates the membrane or the electrospun fabric of the covering without irreversibly damaging the covering or the fabric. In this regard, it is possible for individual pores of the fabric to substantially widen or enlarge.

It has been shown that the electrospun fabric is sufficiently flexible for the pores present in the electrospun fabric or one pore can be widened elastically by the delivery means when the delivery means penetrates the electrospun fabric. In this regard, the pores are deformed or the pore is deformed and the material of the membrane around the pore/pores deforms elastically in a manner such that a sufficiently large opening is generated for the delivery means. The delivery means itself has a diameter which is orders of magnitude larger than the diameter of the pores. The electrospun fabric or the porous membrane is elastic in a manner such that a sufficient deformation of the pores is possible to enable the delivery means to pass through.

An aforementioned exemplary order of magnitude for the diameter of the delivery means is on the basis of pore sizes (inscribed diameter) for the covering or the cover of 5-20 μm for a 1-minute spun mesh structure or pore sizes (inscribed diameter) of 1-5 μm for a 2-minute spun mesh structure.

The external diameter of the suitable delivery means, for example a guidewire with the following microcatheters, may be described as follows in this regard:

External diameter of the guidewire: approximately 0.36 mm (0.014")

External diameter of the microcatheter: approximately 2.1 Fr (0.70 mm)

Internal diameter of the microcatheter (ID): approximately 0.42 mm (0.0165")

Smaller combinations of external diameter for the guidewire of approximately 0.254 mm (0.010") and external diameter of the microcatheter of approximately 1.5 Fr (0.5 mm), ID: 0.33 mm (0.013") are possible.

The aforementioned dimensional ratios are by way of example. Other dimensional ratios of pores and delivery means are possible.

In this state, i.e. when the delivery means penetrates the membrane, the porous membrane of the covering or of the electrospun fabric lies against the outer circumference of the delivery means and therefore seals it against the vascular malformation, in particular the aneurysm. The embolisation means can then be transported via the delivery means through the membrane into the aneurysm. In this regard, the delivery means is disposed in the lumen of the covering device or the stent. Because of the membrane function of the covering or of the fabric, it is possible for the embolisation means to be introduced with the aid of the delivery means through the lumen of the covering device radially or at an acute angle from inside to outside through the wall or the mesh structure of the covering device and into the aneurysm.

Sealing of the delivery means by the fabric or the covering prevents the embolisation means from gaining access to the blood vessel when it is introduced into the aneurysm.

After the aneurysm has been sufficiently filled with the embolisation means, the delivery means can be removed from the mesh structure through the lumen. In this regard, again, the flexibility of the covering or of the electrospun fabric is of assistance, which enables removal of the delivery means, at the same time without letting the embolisation means escape from the aneurysm.

The membrane function of the covering or of the fabric can be described as follows. The covering or the fabric is on the one hand slightly porous, in a manner such that in the implanted state of the covering device, the embolisation means is retained in the aneurysm by means of the covering. On the other hand, the covering or the fabric is open-pored and flexible in a manner such that a delivery means, for example a microcatheter, can be guided through the covering or through the fabric without the covering or the fabric being destroyed thereby or released from the stent support structure, or in general from the mesh structure.

In an electrospun fabric, pores are usually irregular in shape. However, the production method does not permit pores to be produced with a specific arrangement or shape. In fact, the pore size can only be adapted by the process parameters to the extent that it is ensured that at least a portion of the pores have a certain minimum size.

As an example, the electrospinning process may be carried out directly on the mesh structure, so that a bond with the mesh structure is produced at the same time as the covering is formed. The covering may be mechanically interlocked with the mesh structure. As an example, the covering may be bonded to the mesh structure by means of an adhesive bond. The adhesive bond may be produced by means of a bonding agent. The bonding agent may, for example, comprise or consist of polyurethane.

Furthermore, the covering produced from an electrospun fabric is extremely thin and flexible, which has an only slight or zero impact on the flexibility of the mesh structure. In particular, the covering barely inhibits compression of the mesh structure, which is in contrast to prior art coverings which are produced from textile materials. Overall, then, the entire covering device can be compressed to a considerably smaller cross sectional diameter, and thus can be fed via small catheters into particularly small blood vessels. This is of particular relevance for the treatment of aneurysms in cerebral blood vessels; the invention is particularly suitable for this purpose.

Thus, treatments are also possible using the medical set in accordance with the invention in blood vessels which could not be accessed with medical devices of the prior art which have a mesh structure and a covering. Because of the high compressibility of the device, very low delivery forces are generated when delivering by means of a catheter. In particular, the delivery forces in the case of the covering device may be the same as when delivering a mesh structure without a covering.

Furthermore, by means of the covering device which is appropriately disposed at the treatment site, i.e. at the level of the aneurysm, escape of the coil from the aneurysm during and after positioning of the coil can be prevented, so that the risk of occlusion of the vessel caused by the coils may also be at least greatly reduced, and preferably eliminated.

The covering is porous and in particular, it is perfusible. The term "porous" as used here should be understood to mean that the covering or the electrospun fabric is net-like or in the form of netting. This is based on the idea that cells in the region of the covering can be supplied with blood and therefore with nutrients so that in this manner, no underperfusion occurs during placement of the coils or afterwards.

The medical set in accordance with the invention therefore enables an aneurysm to be screened off well in order to retain the embolisation means placed in the aneurysm, for example coils, but at the same time allows nutrients to be supplied to the aneurysm. The supply of nutrients to branching blood vessels and neighbouring inner vessel walls is also achieved by means of the medical set which is covered by the covering. The covering which is formed from the electrospun fabric enables an aneurysm to be covered, but at the same time allows a certain permeability for blood. This permeability is advantageous in order to supply the cells of the aneurysm wall with nutrients. In this manner, degeneration of the cells and a possible resultant rupture of the aneurysm is avoided.

The advantages of the invention do not only derive from the treatment of aneurysms, but also derive from the treatment of other vascular malformations such as fistulas, for example, carotid direct cavernous fistulas being an example.

The invention has various other advantages.

The introduction of coils or liquid embolics can only be planned ahead in conventional treatment methods, for example with flow diverters. In this regard, usually, a second catheter is initially introduced into the aneurysm before the stent or flow diverter is placed in front of the neck of the aneurysm and over the second catheter. The second catheter is located radially outside the stent or the flow diverter between the catheter wall and the vessel wall. Coils or liquid embolics can then be guided through the second catheter into the aneurysm. When the aneurysm has been sufficiently filled, the second catheter is removed.

Later coils or delivery of liquid embolics is no longer possible, because the aneurysm can no longer be accessed without the second catheter.

In contrast, the invention has the advantage that the electrospun fabric assumes the function of a membrane. This provides greater room for manoeuvre for the user, either directly upon application or even months or years later:

The covering device which is covered with the electrospun fabric, in particular the covered stent, is initially placed over the neck of the aneurysm. Next (or if necessary at a later point in time), the delivery means, in particular a microcatheter which has already been used for the delivery of the stent, is used for the passage through the covered layer of fabric. To this end, as an example, a guidewire, preferably in the stiff 0.014" or 0.012" or 0.010" version, is placed in the microcatheter and prior to this is shaped correctly at the tip (for example bent through 90°, narrow radius). Now, any stent cell, in general, for example, a cell of the mesh structure which covers the neck of the aneurysm, is perforated with the guidewire. If the cell has been successfully perforated, the microcatheter behind it on the guidewire can be pushed through the cell into the aneurysm. Next, the guidewire is removed so that coils or liquid embolics can be delivered through the catheter.

In this regard, the fabric reacts like a membrane which lies closely around the guidewire or microcatheter and at the same time prevents embolisation means, for example coils or embolic, from escaping into the blood vessel.

Introducing the embolisation means into the aneurysm with the set in accordance with the invention is carried out chronologically after implanting the covering device. The time interval may vary, and may even be months or years. A second catheter which was required prior to implanting the covering device, is dispensed with. Optionally, the microcatheter may be used directly after placing the stent in order to perforate the membrane and to deliver the liquid embolic or, in general, the embolisation means. Thus, the invention considerably facilitates introduction of the embolisation means into the aneurysm, because implantation of the covering device and introduction of the embolisation means into the aneurysm can be carried out using one and the same delivery means.

According to the claims, the combination of the set in accordance with the invention with the delivery system is disclosed and claimed.

The covering device in accordance with the claims is disclosed independently of the embolisation means and the delivery means. The covering device in accordance with the invention according to the claims is therefore neither limited to the embolisation means nor to the delivery means.

Preferred embodiments, further embodiments and variations form the subject matter of the dependent claims.

Thus, the porous membrane of the covering may therefore be adapted to at least partially contract an opening formed by the delivery means when the membrane is penetrated following removal of the delivery means.

After the aneurysm has been sufficiently filled with coils/liquid embolics, the delivery means, in particular the microcatheter, can be safely pulled out of the aneurysm. The properties of the membrane result in immediate closure of the opening in the cell of the mesh structure, in particular the stent cell, in order to prevent escape of coils or liquid embolics into the cerebral vessel. The cell of the mesh structure does not have to be completely occluded in order to have this effect.

In other words, as soon as the delivery means has been completely removed from the aneurysm and therefore has been withdrawn from the covering or the fabric, the covering or the fabric at least partially closes up again. The flexible opening in the covering or fabric which was widened for the delivery means at least partially contracts because of the elasticity of the fabric, so that the fabric forms a substantially closed, albeit also porous, covering which securely restrains the embolisation means disposed in the aneurysm. Thus, the covering forms a porous membrane which can be pierced or penetrated by the delivery means in order to introduce the embolisation means into the aneurysm and which seals it upon introduction. After removing the delivery means, the membrane closes up again in order to retain the embolisation means in the aneurysm in this manner. The seal does not have to be complete in order to be able to retain the embolisation means. In a further preferred embodiment, the porous membrane is adapted to contract the opening by at most 80%, in particular at most 60%, in particular at most 40%, in particular at most 20% of the diameter of the delivery means.

The contracted opening is smaller than the external diameter of the delivery means with which the delivery means has penetrated the membrane.

Preferably, the covering is slightly porous in a manner such that in the implanted state, it retains the applied embolisation means.

Appropriately, the mesh structure comprises or is a shape memory alloy, in particular nitinol or another shape memory alloy, or is preferably formed from a material of this type. The mesh structure may be braided or be produced by laser cutting. For cerebral applications, a braided mesh structure is preferred.

In order to obtain a sufficient flexibility for the covering, it is preferably formed from irregular filaments disposed in the form of netting which have a filament thickness of between 0.1 μm and 3 μm, in particular between 0.2 μm and 2 μm, in particular between 0.5 m and 1.5 μm, in particular between 0.8 μm and 1.2 μm.

Preferably, the filaments may have a filament thickness of at most 2 μm, in particular at most 1.5 μm, in particular at most 1 μm, and a filament thickness of at least 0.3 μm.

Appropriately, the covering has a porosity of at most 70%, in particular of at most 50%, in particular at most 40%, in particular at most 30%. This means that the stability of the covering is on the one hand increased in respect of the force of the coils, or in general the embolisation means which, for example, presses on the covering in the state in which it is inserted in the aneurysm. On the other hand, the stability of the covering is advantageously optimized having regard to a fracture strength.

In one embodiment, the covering has a porosity of at least 5%, in particular of at least 10%, in particular of at least 20%, in particular of at least 30%, in particular of at least 40% and in particular of at least 45%. This embodiment embodies the concept that by means of an existing porosity at the level of the aforementioned percentages—as already mentioned above—a supply for side vessels or vessel walls, for example, in the vicinity of the aneurysm during placement of the embolisation means and afterwards is guaranteed.

In addition, because of its porosity, the covering is particularly suitable for microcatheters because the covering is compressible and therefore can be introduced and also withdrawn through the microcatheter up to the treatment site with low frictional forces. The term "microcatheter" as used here should be understood to mean a catheter which has an internal diameter with a value in the range from 0.3 mm to 0.75 mm.

The aforementioned upper and lower limits may be combined into ranges (see also claims 5, 6), insofar as it is reasonable to do so.

In accordance with an appropriate embodiment, the covering extends over the entire circumferential surface of the mesh structure. This means that the aforementioned advantages, in particular as regards the stability of the covering and therefore of the mesh structure, are advantageously optimized.

In accordance with an appropriate further embodiment, the covering extends over a portion, in particular at most 70%, in particular at most 60%, in particular at most 50%, in particular at most 40%, in particular at most 30% of the circumference of the mesh structure. Preferably, therefore, the covering extends over only the treatment site, i.e., for example, over an opening of the aneurysm. This further embodiment ensures that on the one hand, an opening of the aneurysm is sufficiently occluded in order to secure the coils placed therein. On the other hand, this ensures that in particular, cells located at the level of the aneurysm and/or side vessels can be better provided with blood and therefore with nutrients because of the lack of covering.

In accordance with a supplemental or alternative embodiment, the covering extends over at least 80%, in particular over at least 90% and in particular over 100% of the length L of the mesh structure. The length L corresponds to the total length of the covering device, in particular of the implant.

This embodiment is particularly suitable for fusiform or long-necked aneurysms in which a longer section has to be covered. The term "fusiform aneurysms" as used herein should be understood to mean aneurysms which extend over at least 50%, in particular over at least 75% of the total circumference or over the entire circumference of a blood vessel.

In one embodiment, the covering extends over at most 80%, in particular over at most 60% in particular over at most 40% of the length L of the mesh structure, wherein the covering is distanced from the distal and/or from the proximal end of the mesh structure. The length L corresponds to the total length of the covering device, in particular of the implant. By means of the incomplete covering of the cylindrical region of the mesh structure which is formed here, any vessels in the vicinity of the aneurysm, and in particular in the vicinity of the opening of the aneurysm, continue to be perfused, i.e. supplied with blood. This embodiment has been shown to be particularly suitable in the case of aneurysms with neighbouring side branches as well as with smaller aneurysms.

The proximal distance is primarily of significance having regard to the guidewire staying on because of the open proximal cells. When the proximal edge cells are open, i.e. not covered, then, for example, the locking system from the Applicant, what is known as the "Crown Sleeve" of the transport wire, can be safely coupled. For this, an upper limit of 80% coverage is sufficient. Leaving 10% of the total length L per axial side with open edge cells should be sufficient.

In one embodiment, the covering has at least 10 pores with a size of at least 15 $\mu m^2$ over an area of 100000 $\mu m^2$. During production of the covering, the minimum size of the pores can in particular be adjusted by the process time for electrospinning. This combination of a specific minimum number of pores and a minimum size for these pores has been shown to be particularly necessary in practice for a sufficient perfusibility of the covering with good coverage at the same time.

Preferably, the covering is formed by a plastic material, in particular by a polymer and preferably by polyurethane. Materials of this type are particularly light and can readily be produced in fine filaments by means of an electrospinning process. On the one hand, the plastic material can therefore be used to produce a particularly thin and fine-pored covering. On the other hand, the plastic material already has a high intrinsic flexibility, so that a high compressibility of the medical set is obtained. Alternatively, the covering may also be formed by polyethylene or fluoropolymers or, for example, on polycarbonate-based thermoplastic polyurethanes. Furthermore, as an alternative or supplementally, fillers such as anti-thrombogenic substances may be incorporated into the aforementioned materials for the covering, before the covering is formed with them by the electrospinning process. As an alternative or supplementally, the covering is coated with substances of this type, for example with anti-thrombogenic substances.

To this end, the surface of the covering is then in particular provided with a nano-coating.

Preferably, the covering is formed by a plastic material, in particular a polymer, preferably polyurethane, which preferably has a Shore hardness of at least 80 A, in particular at least 90 A, in particular at least 55 D, in particular at least 65 D, in particular at least 75 D. These values for the materials have been shown to be advantageous having regard to the membrane function of the covering.

In a further embodiment, the covering is disposed on an outside and/or on an inside of the mesh structure. In a situation in which the covering is disposed on the outside of the mesh structure, the mesh structure forms a support structure which applies a sufficient radial force in order to fix the covering against a vessel wall. In this regard, the mesh structure supports the externally disposed covering.

As an alternative, or in addition, the covering may be disposed on an inside of the mesh structure. In particular, it is possible for the mesh structure to be incorporated between two coverings which are respectively formed by an electrospun fabric. The mesh elements of the mesh structure may in this manner be completely sheathed by the electrospun fabric. Specifically, it may be provided that the electrospun fabric of a covering extends on the inside of the mesh structure in through the cells of the mesh structure and is connected to the electrospun fabric of a covering on the outside of the mesh structure. The mesh elements which border the cells are therefore sheathed on all sides by electrospun fabric.

In accordance with a preferred embodiment, the mesh structure is formed from webs, which are connected together in one piece, i.e. are monolithic, and delimit closed, in particular diamond-shaped cells. Preferably, the mesh structure has 3 to 9, in particular 4 to 6 cells successively disposed in the circumferential direction, which form a circumferential cell ring.

Thus, in general the mesh structure may be formed as a one-piece mesh structure. In this regard, in preferred embodiments, the mesh elements form webs which are coupled together into one piece by means of web connectors (one-piece mesh structure).

It is also possible for the mesh structure to be formed from wires braided together. The braided wire may consist of a single wire which curves around at the longitudinal ends of the network structure and returns. The wire may be braided with itself in order to form the network structure. The network structure may also consist of a plurality of wires which are braided together. The plurality of wires may be curved and returned at one axial longitudinal end, while the opposite axial longitudinal end may have wire ends which are open. It is also possible for the interwoven wires to have open wire ends at both axial longitudinal ends.

The mesh structure may also comprise a braid which is braided from at least one wire, in particular from a plurality of wires with the formation of meshes, wherein the wire or the wires are movable relative to each other at the points of intersection.

The embolisation means may comprise at least one deformable wire, in particular a coil, and/or a liquid embolic. In the case of a liquid embolic, more specifically, it is a liquid embolic which can be delivered through a microcatheter with an external diameter of at most 2 Fr (internal diameter at most 0.017"/0.43 mm).

The wire may have a radiopaque core material and a sheath material produced from a shape memory alloy. In particular, the volume ratio between the core material, preferably platinum, and the volume of the whole of the composite wire is between 20% and 40%, in particular between 25% and 35%. While a braided mesh structure is characterized by a particularly high flexibility, in particular bending flexibility, a one-piece mesh structure has comparatively thin walls, so that the mesh structure has a smaller influence on the blood flow inside a blood vessel. The webs furthermore preferably have a thickness with a value in the range between 30 μm and 60 μm. Furthermore, the cells are each delimited by four webs, wherein the basic geometry of the cells is essentially diamond-shaped in the preferred design. In particular, each cell is delimited by two pairs of webs, wherein the webs, which are essentially parallel with respect to each other or opposite each other and not connected directly together, form a web pair. A design of this type has already been described in FIG. 1 and the paragraphs [0041] to [0046] of patent document DE 10 2011 009 371 B3 from the Applicant, to which reference is made in this regard. The webs of a first web pair have a smaller web width than the webs of a second web pair. This arrangement of the webs with different web widths enhances the flexibility of the network structure and therefore facilitates the introduction of the medical device into human vessels, in particular when these vessels are highly tortuous. The enhanced flexibility improves application to the vessel wall and therefore prevents the formation of congestive regions which promote thromboses. The good flexibility and the resulting good introduction capability in and/or by means of the catheter is particularly important in combination with a biological coating, preferably fibrin, preferably fibrin including heparin.

In addition to the pores formed by the electrospinning, the fabric may be perforated, at least in regions, by further pores which are formed in the electrospun fabric by processing the fabric, in particular by laser cutting or thermal widening using a laser. In this manner, a deliberate and, if desired, zonal increase in the porosity or enlargement of the pores may be obtained after the electrospinning process. As an example, laser cut, defined pores or pores thermally widened using the laser beam may be formed on the entire circumference or even on only a portion thereof.

Preferably, the fabric is perforated by the further pores over at least 25%, in particular over at least 40%, in particular over at least 50% of the circumference of the mesh structure. Thus, for example, the region opposite the neck of the aneurysm can be deliberately perforated.

The fabric may be free from further pores to an extent of at least 25%, in particular at least 40%, in particular at least 50% of the circumference of the mesh structure. In other words, a portion of the fabric is not post-processed or subsequently perforated. In this part of the fabric, no other further pores, other than the pores formed by electrospinning, are introduced into the fabric. In this region, the fabric consists of only the pores formed by electrospinning. The region of the fabric which is free from further pores may be disposed in the region of the neck of the aneurysm when in the implanted state. This may be desired, for example, when an unaltered porosity of the electrospun fabric is advantageous to the treatment of the aneurysm.

A combination of regions of unaltered electrospun fabric and subsequently perforated electrospun fabric is possible.

The further pores may be formed in both axial directions outwards from the axial centre of the mesh structure. In a further exemplary embodiment, additional pores may be disposed proximally or distally within the covering or the fabric.

The length over which the further pores may be distributed corresponds to at least 25% of the axial length of the covering or the fabric, in particular at least 30%, in particular at least 40%, in particular at least 50% of the axial length of the covering or the fabric.

In order to promote perfusion, the size of the further pores may be at least 50 μm, in particular at least 100 μm, in particular at least 200 μm, in particular at least 300 μm.

Regarding the geometry of the subsequent pore widening, it can additionally be stated that the shape of the further pores may be round or oval. It is also possible for the further pores not to have a recognisable master shape.

The separations of the further pores with respect to each other having regard to the diameter of the further pores may be at least 1 time the distance, in particular at least 1.5 times the distance, in particular at least 2 times the distance, in particular at least 2.5 times the distance. In the case of 1 time the distance, this therefore corresponds to the diameter of a further pore.

In a particularly preferred embodiment, the circumferential contour of the covering is marked by a radiopaque means, at least in sections, in particular entirely circumferentially. This may, for example, be obtained by using radiopaque wires which are braided into the mesh structure along the contour of the covering. It is also possible to obtain the contour of the covering by means of an array of radiopaque sheaths, for example Pt—Ir sheaths or crimped C sheaths.

The site of the covering or of the fabric is therefore visible under X rays, so that the physician can securely position the device—even in the correct rotational position.

The fabric per se may have a radiopaque means. As an example, the filaments of the fabric may be filled with a radiopaque material, in particular with at least 10% to a maximum of 25% of radiopaque material, for example barium sulphate, $BaSO_4$. The base colour of the filaments of the fabric may be transparent; upon adding barium sulphate, $BaSO_4$, these can appear white/yellowish.

In an ancillary aspect, the invention concerns a medical system for the treatment of aneurysms with a medical set. The set is the medical set which has already been described above. The system furthermore comprises a delivery means, in particular a microcatheter, with which the covering can be perforated in order to introduce the embolisation means.

Appropriately, in the expanded state, the cells of the mesh structure have an inscribed diameter or can be expanded to an inscribed diameter which corresponds to at least the external diameter of the delivery means. The inscribed diameter is the diameter of the largest possible circle which can be inscribed inside the pores. In other words, the inscribed diameter of the pores corresponds to the external diameter of a cylinder which can just be pushed through the pore. If the delivery means, in particular the catheter is not orientated at an angle of 90° to the pore of the covering, upon application, an oval opening is made which takes up a larger area.

In particular in the embodiment of the medical system described above, this ensures that the delivery means can easily be introduced into the aneurysm through the covering or the fabric.

Preferably, the embolisation means are formed by a deformable wire, in particular a coil wire, in particular by a coil as mentioned hereinabove, or by a liquid, for example a hydrogel. Embodiments of the embolisation means of this type have been shown to be particularly suitable having regard to a treatment of aneurysms.

The advantages and preferred embodiments set out in respect of the medical set are applicable to the medical system, and vice versa. All of the dimensional information given in respect of the medical set and in respect of the medical system are given with respect to the expanded state of the mesh structure, unless stated otherwise.

The invention will now be described in more detail with the aid of exemplary embodiments made with reference to the accompanying diagrammatic drawings.

In this regard, FIGS. 1 to 8 show the use of a medical set according to an exemplary embodiment in accordance with the invention, wherein the embolisation means is a coil. FIGS. 9 to 16 show a further possibility of the use of the medical set according to an exemplary embodiment in accordance with the invention, wherein the embolisation means is a liquid embolic.

BRIEF DESCRIPTION OF THE DRAWINGS

Specifically, in the figures.

In the figures, identical parts are shown with identical reference numerals.

DESCRIPTION

Figure 1:
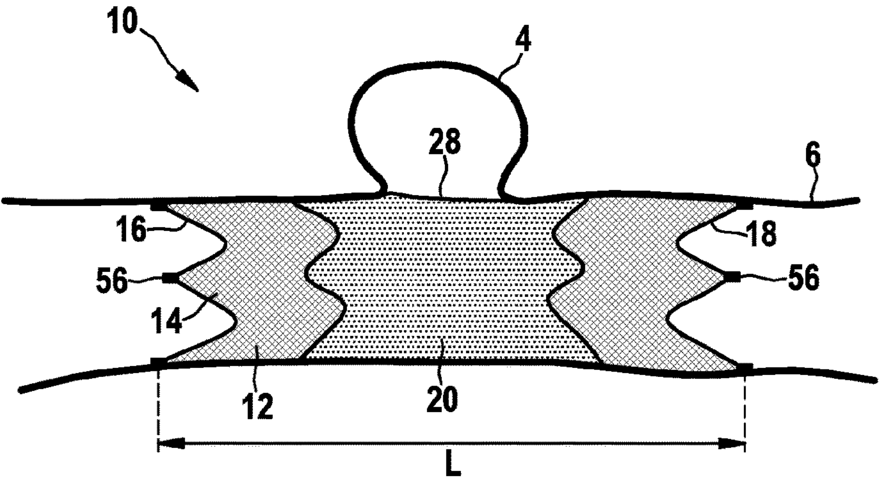
FIG. 1 shows a side view of a covering device of a medical set in accordance with the invention according to a first embodiment in the implanted state (step 1)

The medical set 2 which is shown diagrammatically in FIGS. 1 to 8 serves for the treatment of aneurysms 4, or in general of vascular malformations such as fistulas, for example, and is shown in FIG. 1 in a state in which it is disposed in a vessel 6.

The medical set 2 has a covering device 12 which can be moved through a catheter (not shown) to a treatment site 10. The treatment site 10 is preferably a site along the vessel 6 at which the aneurysm 4 is formed. The covering device 12 serves to permanently cover the aneurysm 4. This means that the covering device 12, after it has been completely released from the catheter, can no longer be withdrawn into it but remains permanently in the vessel. Specifically, the covering device 12 is a permanent implant, in particular a stent.

Permanent covering devices are distinguished from temporary covering devices which are removed from the vessel again following treatment. A further distinguishing feature of the permanent covering device is the releasable connection to the transport wire, which is necessary in order to be able to uncouple the covering device or mesh structure from the delivery system after the delivery means has completely left the delivery means. This is not the case with temporary covering devices, which are securely connected to the transport wire in order to be contracted into the delivery means.

The covering device 12 comprises a self-expandable mesh structure 14. To this end, the mesh structure 14 is preferably produced from a shape memory material. The mesh structure 14 is tubular in shape or in the shape of a hollow cylinder and is open at the proximal longitudinal end 16 and at the distal longitudinal end 18. This means that at both longitudinal ends 16, 18, the mesh structure 14 has a cross section of flow which is free from the mesh structure 14. The cross section of flow is the cross section through which a flow can pass which is transverse to the longitudinal axis of the mesh structure 14 which is delimited radially outwardly by the vessel or by the mesh structure 14. This distinguishes permanently implantable covering devices or the mesh structure 14 from the mesh structure 14 of a temporarily implantable covering device, in which the mesh structure protrudes into the cross section of flow in the manner of a funnel at least at the proximal longitudinal end. In the case of the permanently implantable covering device 12, in contrast, the mesh structure 14 lies against the vessel wall along the entire length and applies a radial force to it.

Furthermore, at least a portion of the mesh structure 14 is provided with a covering 20. The covering 20 is produced from an electrospun fabric and forms a porous membrane. The electrospun fabric is adapted in a manner such that it endows the covering with a membrane function. The porous membrane is formed in a manner such that it can be penetrated by the delivery means for the application of the embolisation means. In addition, the membrane is adapted so that in the penetrated state, the membrane lies against the outer circumference of the delivery means.

This is the case with all of the coverings 20 in this application.

There are a number of possible forms for the covering 20.

As an example, as can be seen in FIGS. 1 to 16, the covering 20 may extend along part of the length of the mesh structure 14 or over a portion, in particular over at most 80%, in particular over at most 60% and particularly especially over at most 40% of the total length L of the mesh structure 16. The total length L of the mesh structure is shown in the figures and extends between the outermost axial longitudinal ends along the central line of the mesh structure.

This means that in the implanted state, the covering 20 is located only within the region of the opening 28 of the aneurysm 4, so that cells and/or side vessels bordering the aneurysm 4 are not covered by the covering 20. In this manner, the cells and/or the side vessels can still be supplied with blood and therefore with nutrients because of the mesh structure 14 formed with cells.

As can clearly be seen in the figures, the covering 20 is substantially centrally disposed, i.e. in the region of the axial centre of the mesh structure 14. In other words, the longitudinal axial ends of the covering 20 are approximately equidistant from the proximal and distal longitudinal ends 16, 18 of the mesh structure 14.

The contour of the longitudinal ends of the covering 20 which extends in the circumferential direction of the mesh structure 14 substantially corresponds to the contour of the proximal and distal longitudinal ends 16, 18 of the mesh structure. This feature is disclosed and claimed both in connection with the specific exemplary embodiments as well as in general in connection with other exemplary embodiments which are not shown here.

Figure 17:
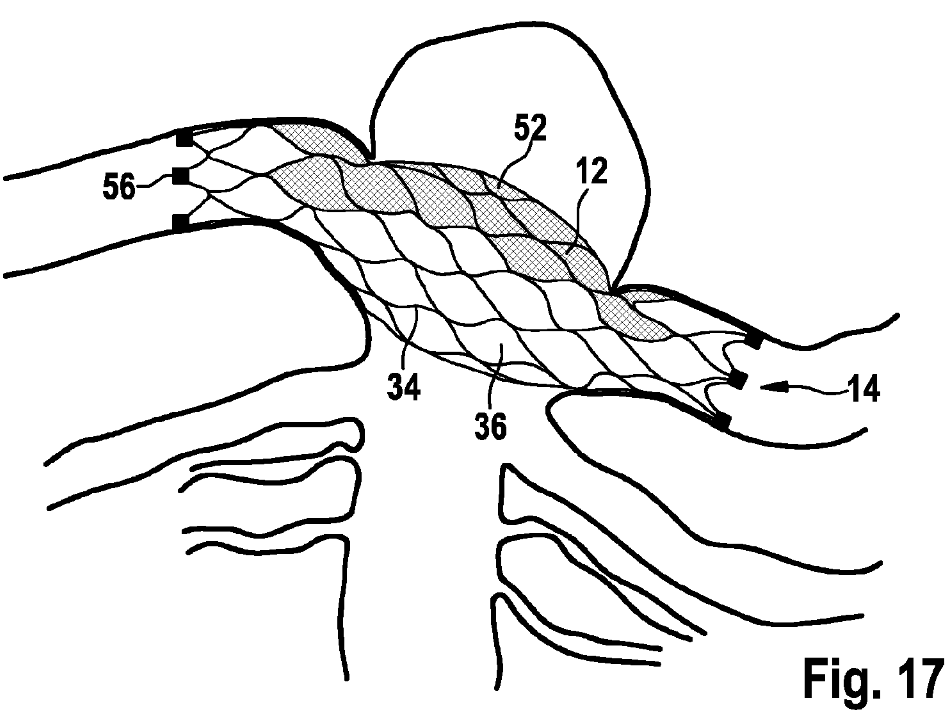
FIG. 17 shows a side view of a covering device of a medical set in accordance with the invention according to a further embodiment, in the implanted state.
Figure 18:
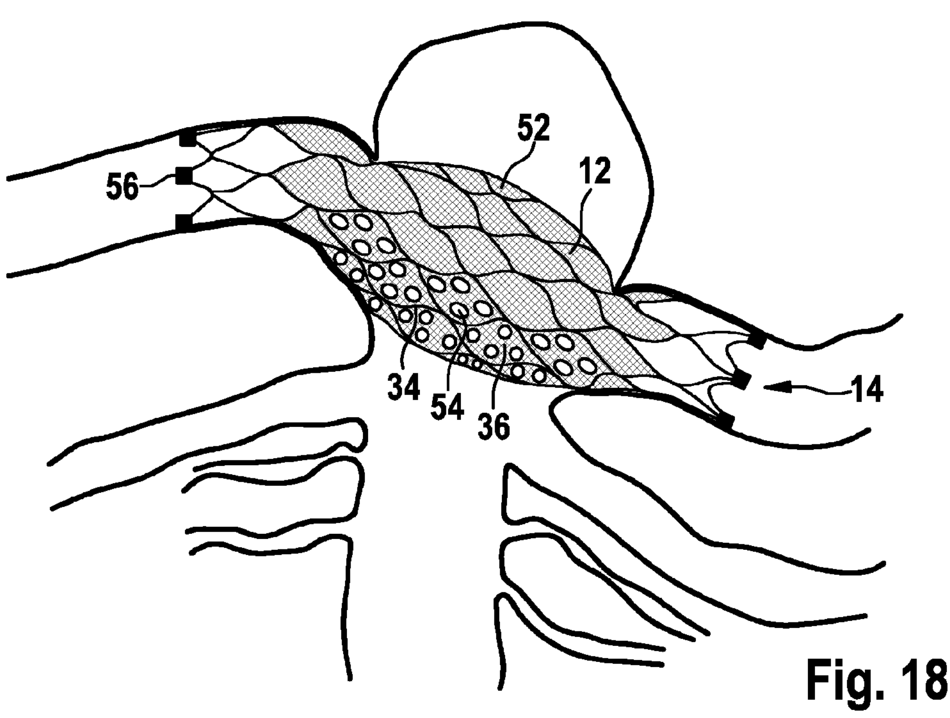
FIG. 18 shows a side view of a covering device of a medical set in accordance with the invention according to a further embodiment, in the implanted state.

The coverings 20 shown in the figures extend over the total circumference of the mesh structure 14. It is also possible, as shown in FIGS. 17, 18, for example, for the covering 20 to cover only a segment of the mesh structure 14 in the circumferential direction, i.e. an angular segment.

In this regard, the covering 20 serves, in particular when an embolisation means 40 is placed inside the aneurysm 4, to prevent the embolisation means 40 from escaping from the aneurysm 4 following placement, until the blood inside the aneurysm 4 has been clotted by the embolisation means 40 and therefore the aneurysm 4 has been reliably occluded.

FIGS. 1 to 8 are used to explain how the corresponding exemplary embodiment of the medical set comprising the covering device 12 and the embolisation means 40 is used for the treatment of an aneurysm. The treatment of other vascular malformations is possible in a corresponding manner.

FIG. 1 shows the covering device 12, for example in the form of a stent, in the permanently implanted state, i.e. after complete release from the delivery system (step 1). The covering device 12 with the covering 20 is disposed over the aneurysm opening 28. The covering 20 covers the aneurysm opening 28. The X-ray markers 56 at both axial longitudinal ends 16, 18 mark the position of the covering device 12.

Figure 2:
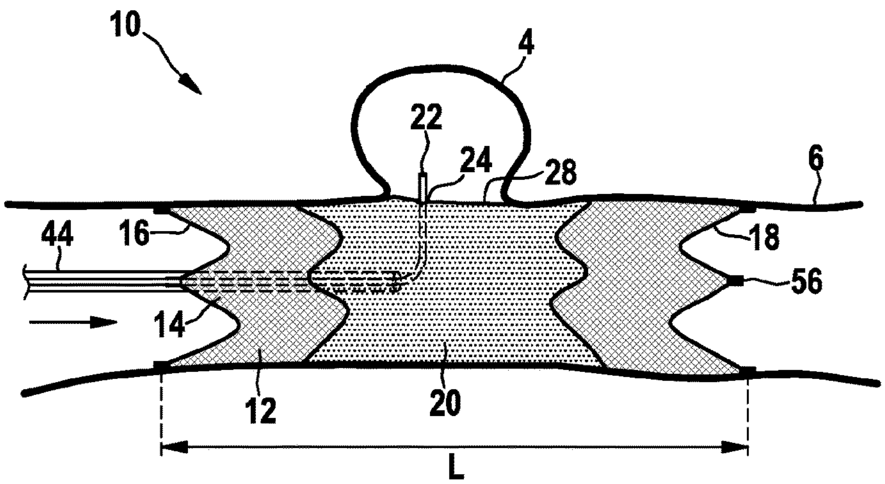
FIG. 2 shows a side view of the covering device according to FIG. 1 with a delivery means and a guidewire which penetrates the covering of the covering device (step 2)

As can be seen in FIG. 2, in step 2 a delivery means 44 in the form of a microcatheter is introduced through the lumen of the covering device 12. To this end, in a manner which is known per se, a guidewire 22 is also disposed in the lumen of the covering device 12 through which the delivery means 44 is guided to the treatment site. The guidewire 22 penetrates the covering 20 in the region of the aneurysm opening 28, as can clearly be seen in FIG. 2. In this regard, the membrane function of the covering 20 comes to the fore. This enables perforation or expansion or widening of the pores of the covering by means of the guidewire 22 because of the pores formed through the electrospun fabric. The guidewire 22 penetrates the material of the covering 20, wherein the corresponding pore or pores which are penetrated by the guidewire 22 is or are widened. This forms the opening 24 through which the guidewire 22 is pushed into the interior of the aneurysm 4.

Figure 3:
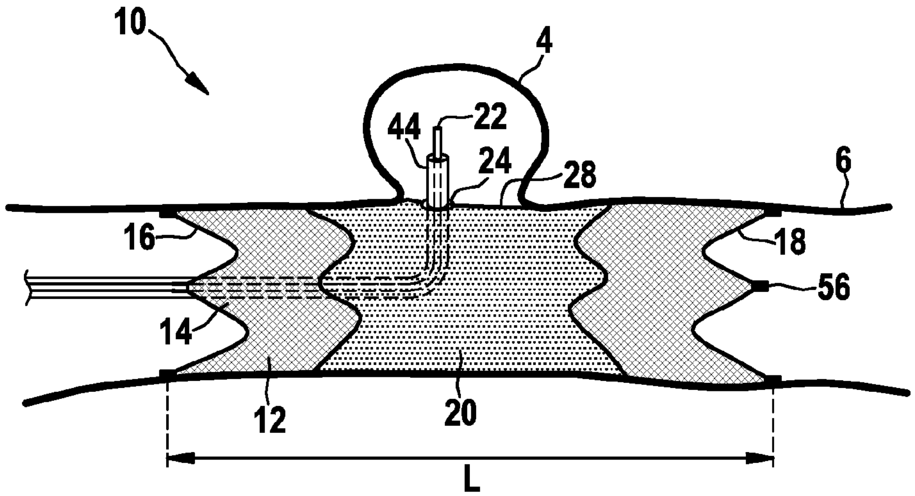
FIG. 3 shows a side view of the covering device according to FIG. 1, wherein the delivery means penetrates the covering (step 3)

FIG. 3 shows that the delivery means 44 is pushed further forwards into the aneurysm 4 via the guidewire 22. In this state, the delivery means 44, specifically the distal free end of the delivery means 44, protrudes into the aneurysm 4. In doing this, the delivery means 44 penetrates the covering 20 in the region of the opening 24 which has already been formed by the guidewire 22. The opening 24 is widened further by the delivery means 44 to the external diameter of the delivery means 44. The widened opening 24 lies closely alongside the outer contour of the delivery means 44 and therefore seals the aneurysm 4 against the lumen of the covering device 12.

This is made possible by the membrane-like construction of the covering 20, specifically by the electrospun fabric which has an elasticity such that the material around the penetrated pore/the penetrated pores or around the opening 24 are sufficiently elastically deformed.

Figure 4:
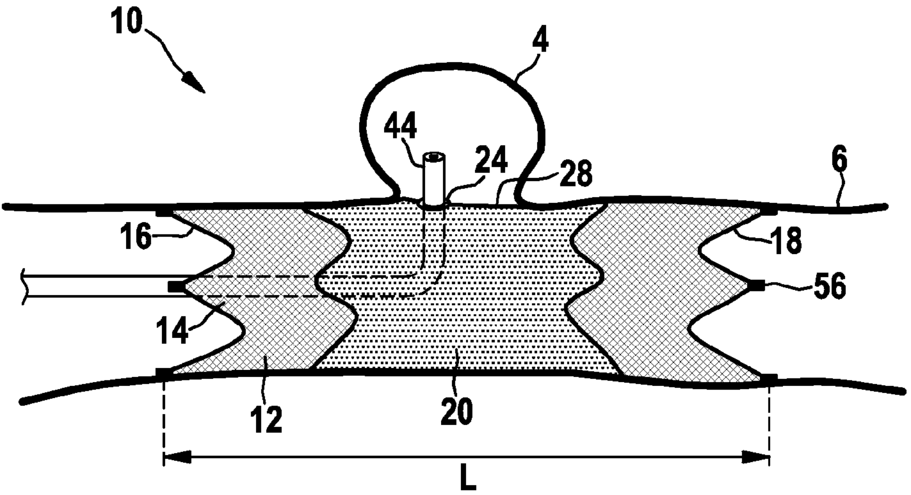
FIG. 4 shows a side view of the covering device according to FIG. 1, wherein the guidewire has been contracted (step 4)

In accordance with FIG. 4, in step 4, the guidewire is withdrawn from the delivery means 44 so that the free end of the delivery means 44 is placed in the aneurysm 4 and has a free lumen for the application of the embolisation means 40.

Figure 5:
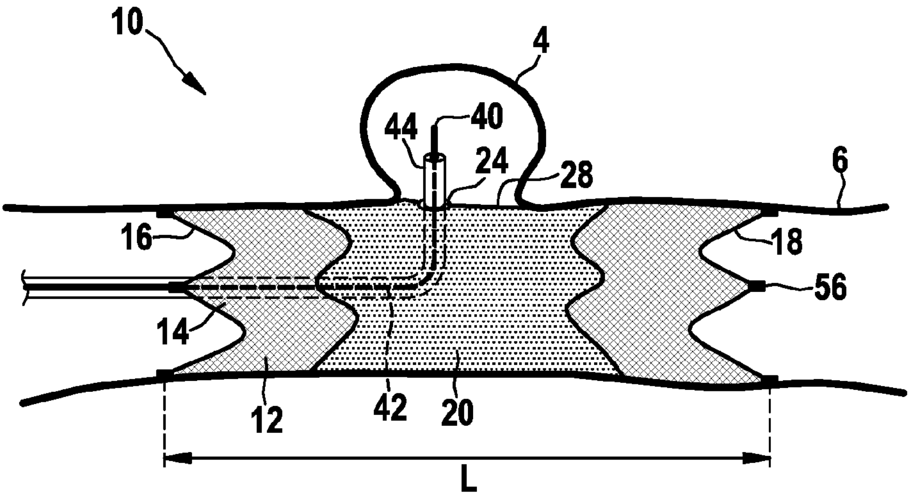
FIG. 5 shows a side view of the covering device according to FIG. 1, wherein a coil wire has been pushed through the delivery means (step 5)
Figure 6:
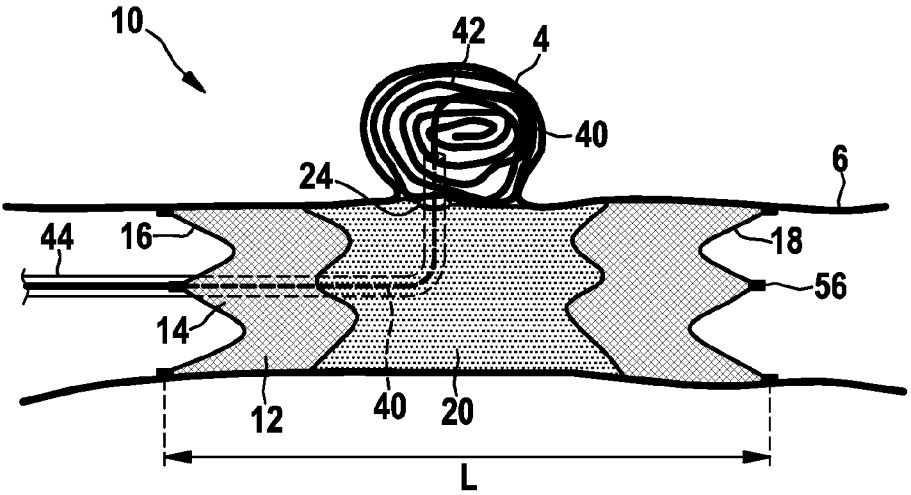
FIG. 6 shows a side view of the covering device according to FIG. 1, wherein the coil wire has been introduced into the aneurysm (step 6)

FIG. 5 shows that in step 5, the embolisation means 40, specifically a coil wire 42, is delivered to the aneurysm through the delivery means 44 and the opening 24 in the covering 20.

In step 6, as can be seen in FIG. 5, the aneurysm 4 is filled with the embolisation means 40 or the coil wire 42. In this state, the covering 20 already retains the embolisation means 40 in the aneurysm. In addition, the covering 20 seals the aneurysm 4 in the region of the opening 24 against the lumen of the covering device 12, because the opening 24 lies closely alongside the external diameter of the delivery means 44. Escape of the embolisation means 40 is therefore avoided because of the application.

Figure 7:
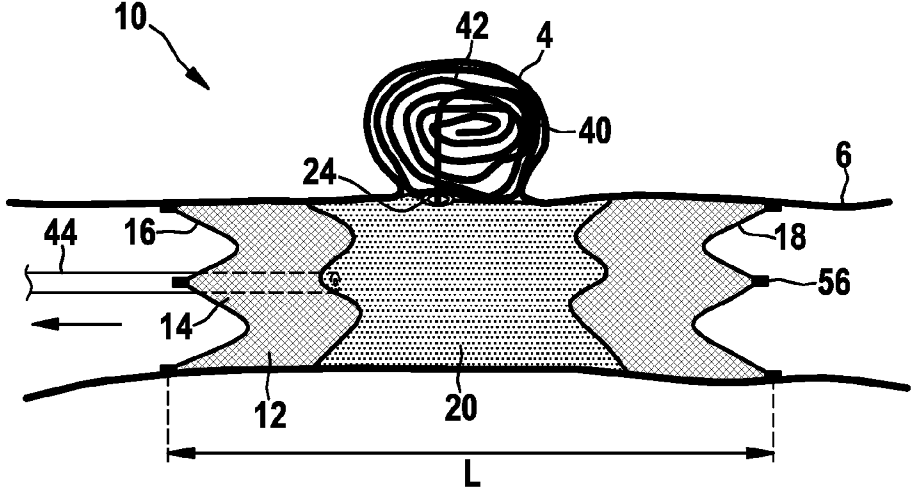
FIG. 7 shows a side view of the covering device according to FIG. 1, wherein the delivery means has been removed from the vessel and the remaining opening has been made substantially smaller after removal of the delivery means (step 7)

After the aneurysm has been sufficiently filled with the embolisation means 40, the delivery means 44 is removed from the lumen of the covering device 12, as can be seen in FIG. 7 (step 7). FIG. 7 clearly shows that the opening 24 contracts. The contracted opening 24 has a smaller diameter than the external diameter of the delivery means 44. This means that the embolisation means 40 is securely retained in the aneurysm 4. It is not absolutely necessary for the opening 24 to be completely contracted and the original pore size is regained. It is sufficient for the opening 24 to contract far enough for the contracted opening 24 to prohibit the embolisation means 40 from gaining access to the lumen of the covering device 12. The coils/hydrogels or, more generally, the embolisation means delivered through the delivery means correspond to approximately the internal diameter of the delivery means. When the opening becomes smaller after removal of the delivery means, the embolisation means, i.e. the coil or the hydrogel cannot escape through the opening.

Figure 8:
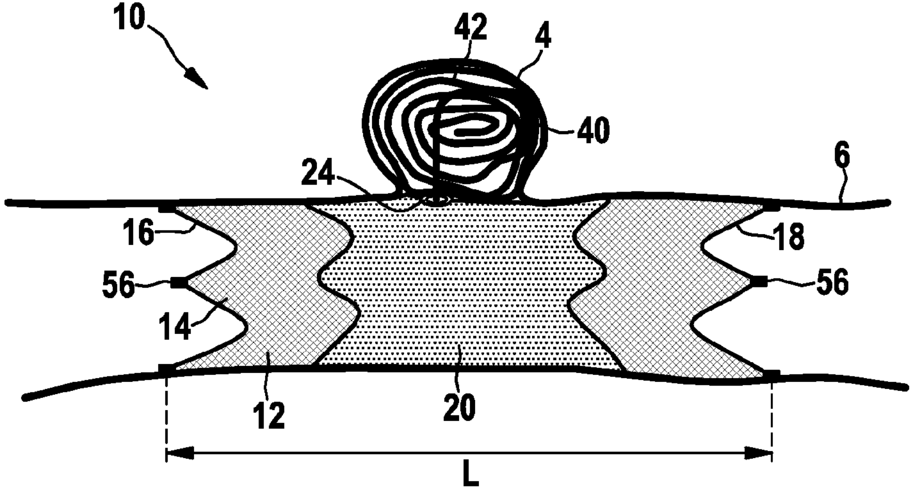
FIG. 8 shows a side view of the covering device according to FIG. 1 in the final state, wherein the covering retains the coil wire disposed in the aneurysm and the remaining opening has been made substantially smaller after removal of the delivery means (step 8)
Figure 9:
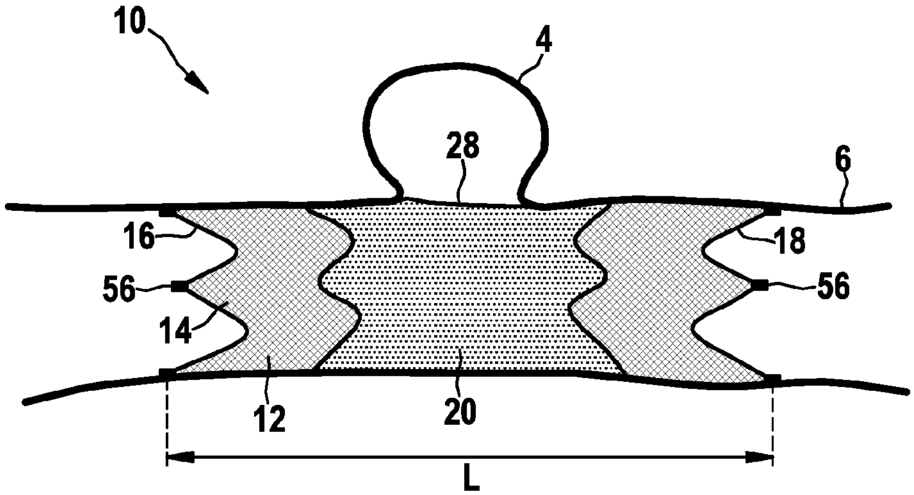
FIG. 9 shows a side view of a covering device of a medical set in accordance with the invention according to a second embodiment in the implanted state (step 1)
Figure 10:
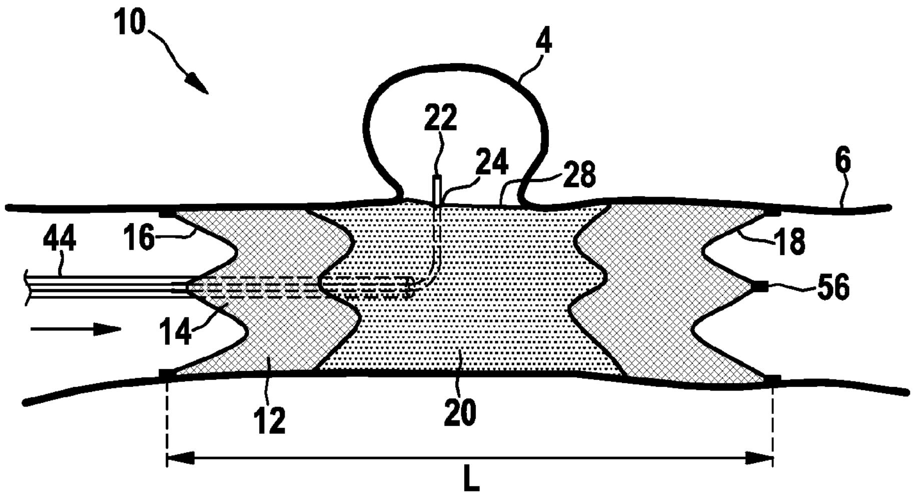
FIG. 10 shows a side view of the covering device according to FIG. 9 with a delivery means and a guidewire which penetrates the covering of the covering device (step 2)
Figure 11:
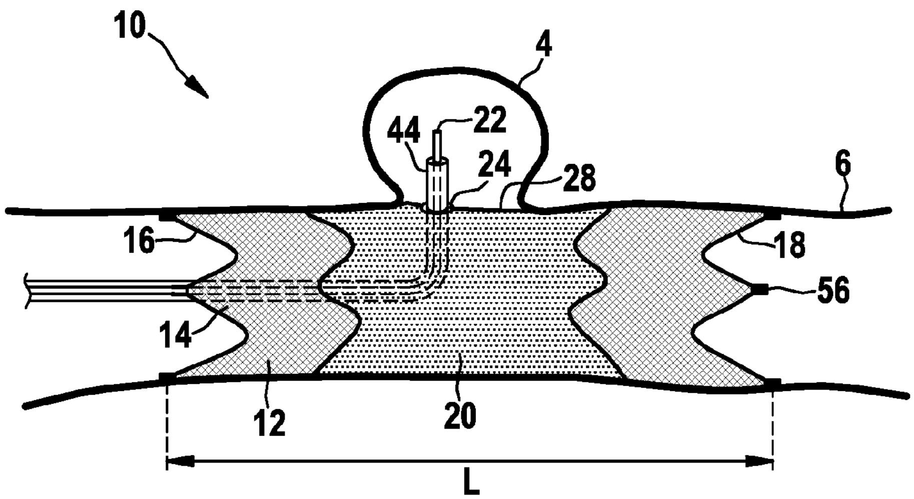
FIG. 11 shows a side view of the covering device according to FIG. 9, wherein the delivery means penetrates the covering (step 3)
Figure 12:
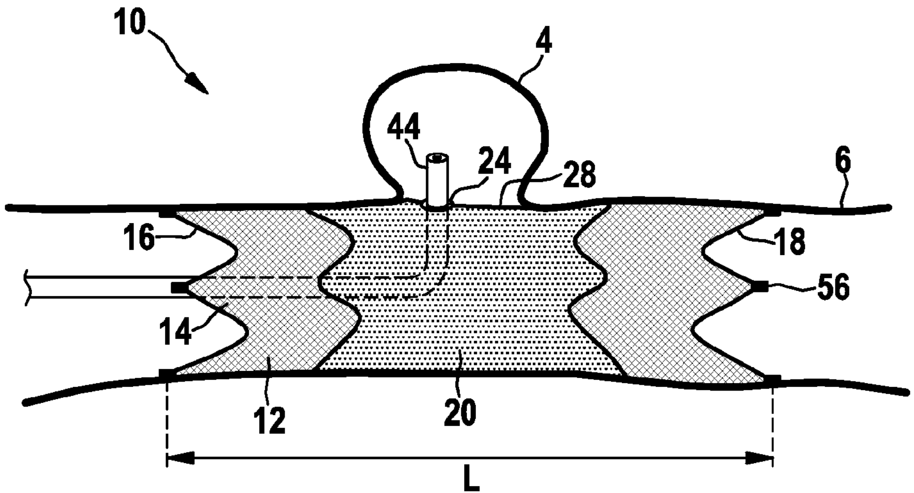
FIG. 12 shows a side view of the covering device according to FIG. 9, wherein the guidewire has been contracted (step 4)
Figure 13:
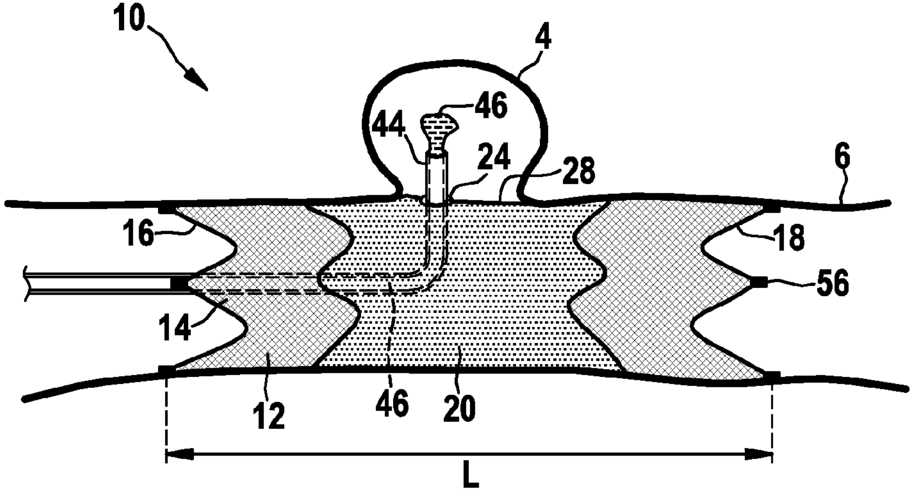
FIG. 13 shows a side view of the covering device according to FIG. 9, wherein an liquid embolic has been transported through the delivery means (step 5)
Figure 14:
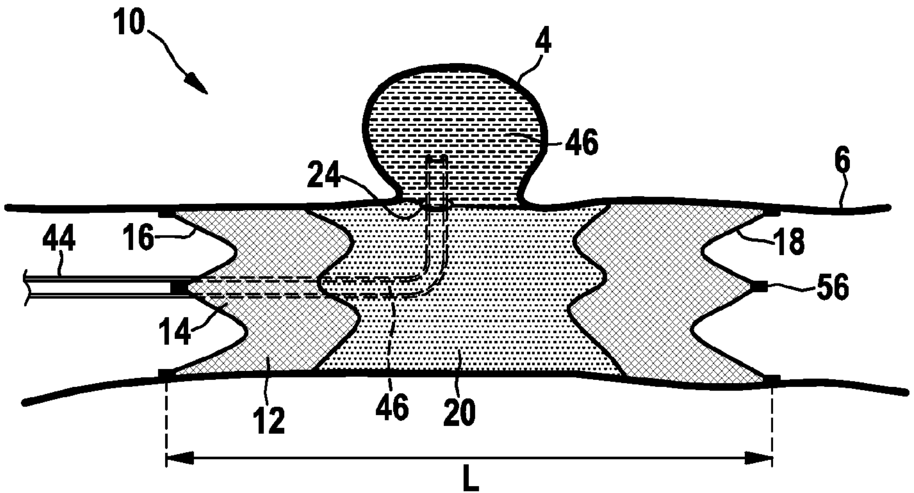
FIG. 14 shows a side view of the covering device according to FIG. 9, wherein the liquid embolic has been introduced into the aneurysm (step 6)
Figure 15:
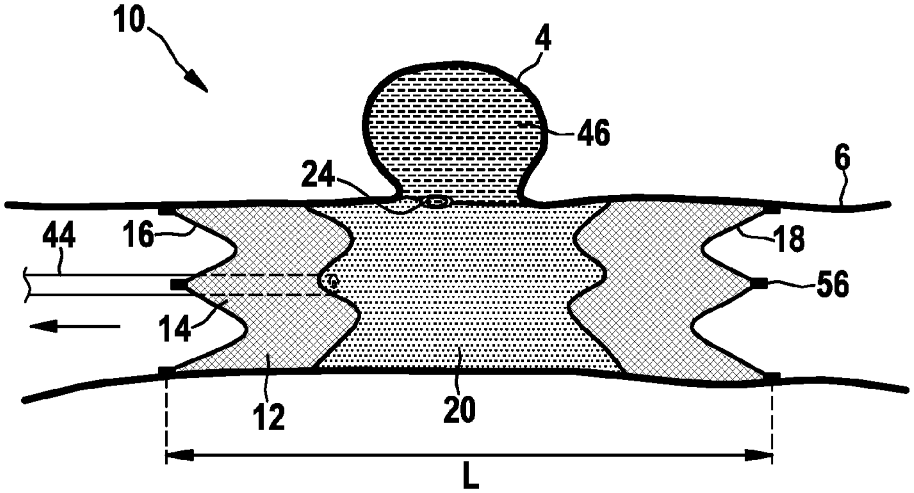
FIG. 15 shows a side view of the covering device according to FIG. 9, wherein the delivery means has been removed from the vessel and the remaining opening has been made substantially smaller after removal of the delivery means (step 7)
Figure 16:
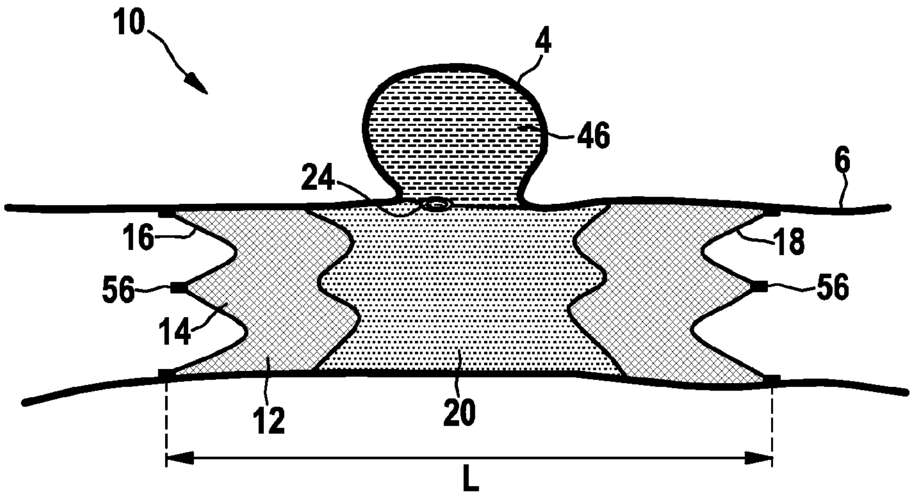
FIG. 16 shows a side view of the covering device according to FIG. 9 in the final state, wherein the covering retains the liquid embolic disposed in the aneurysm and the remaining opening has been made substantially smaller after removal of the delivery means (step 8)

FIG. 8 shows the final state after the delivery means 22 has been completely removed and the covering device 12 retains the embolisation means 40 in the aneurysm 4.

It is possible to carry out steps 1 to 8 in the same operation, i.e. in chronological succession and contiguously. It is also possible to initially implant only the covering device, as can be seen in FIG. 1, without initially carrying out steps 2 to 8. If it turns out that the treatment outcome is not yet sufficient, then the treatment of the aneurysm with an embolisation means 40 can be carried out at a later time without problems. This means that in a second, chronologically later operation, steps 2 to 8 may be carried out. The medical set comprising the covering device and the embolisation means therefore enables flexible and appropriate methods for the treatment of aneurysms to be carried out.

A further exemplary embodiment is shown in FIGS. 9 to 16. This exemplary embodiment is distinguished from the exemplary embodiment of FIGS. 1 to 8 in that instead of the coil wire 42, another embolisation means 40 is used, namely a liquid embolic 46. The application of the liquid embolic 46 is carried out, in similar manner to the application of the coil wire 42. In this regard, reference should be made to the discussions regarding FIGS. 1 to 8.

In this exemplary embodiment, the opening 24 is contractable in a manner such that after removing the delivery means 44, an opening remains in the covering 20 which is sufficiently small to prevent the liquid embolic 46 from escaping. Here again, the opening 24 does not have to be completely closed in order to achieve the desired result.

FIG. 17 shows the mesh structure 14 of an exemplary embodiment in accordance with the invention in the implanted state, wherein the covering 20 is disposed on the mesh structure 14 in the region of the neck of the aneurysm and covers it. The covering 20 is disposed on a portion of the circumference or on an angular segment of the mesh structure 14. In this example, the fabric or the covering 20 covers approximately half the circumference of the mesh structure 14 or stent. Another degree of coverage, i.e. more or less than half the circumference of the mesh structure 14, is possible.

In this manner, perfusion of cells and/or side vessels neighbouring the aneurysm 4 is further optimized, because in this manner, preferably, only the opening 28 of the aneurysm 4 is covered and also, cells and/or side vessels at the same level as the aneurysm can still be supplied with blood and nutrients. In this manner, for example, a side vessel which is disposed opposite the aneurysm 4 can be supplied with blood.

As can be seen in FIG. 17—in contrast to FIG. 18—no pores other than the pores formed by electrospinning are provided in the fabric. The properties of the fabric are therefore determined only by the pores formed in the electrospinning production process.

FIG. 18 shows a further exemplary embodiment of the invention, in which the mesh structure 14, as in FIG. 17, is implanted for the treatment of an aneurysm. In contrast to FIG. 17, the covering 20, in particular the fabric, is applied to the entire circumference of the mesh structure 14 and in fact by electrospinning. A portion of the covering 20, specifically the portion of the covering 20 which is opposite to the neck of the aneurysm, is perforated in addition to the pores 52 formed by electrospinning. This is carried out by a post-treatment of the fabric, for example by laser cutting or thermal widening using a laser. The further pores 54 formed in the fabric in this way are larger than the pores formed by the electrospinning, as can be seen in FIG. 18. In the example of FIG. 18, four further pores 54 are formed per cell. The number of the further pores 54 may vary. In contrast to the pores 52 formed by electrospinning, the pores 54 are geometrically defined, for example round. This is made possible because of the laser cutting or thermal widening or thermal melting using a laser.

The additional perforation of the fabric allows for targeted influencing of the perfusibility of the fabric, for example in order to improve the blood supply to side branches, without compromising the treatment of the aneurysm thereby.

As can be clearly seen in FIGS. 17, 18, X-ray markers 56 are provided in the medical set 2 and in particular in the mesh structure 14. The X-ray markers 56 are disposed on the cell tips of the marginal cells of the mesh structure 14. Specifically, the X-ray markers 56 may be formed as radiopaque sheaths, for example produced from platinum or gold, which are crimped onto the cell tips of the marginal cells. FIGS. 17, 18 show that three X-ray markers 56 are disposed on each longitudinal end of the mesh structure 10.

The covering devices 14 in accordance with FIG. 17 and FIG. 18 are combined with an embolisation means 40 to form a medical set. In turn, the set can be combined with a delivery means 44 to form a system.

The aforementioned embodiments, in particular as regards the extent of the covering 20 along a length L of the mesh structure 14 and as regards an extent of the covering 20 along a circumference of the mesh structure 14, may be combined in any configuration and may be combined in any configuration. Thus, for example, an embodiment is also possible in which the covering 20 extends over the entire length L of the mesh structure, but also extends over only a portion of the circumference of the mesh structure 14.

LIST OF REFERENCE INDICATORS

2 medical set
4 aneurysm
6 vessel
8 free
10 treatment site
12 covering device
14 mesh structure
16 proximal longitudinal end
18 distal longitudinal end
20 covering
22 guidewire
24 opening
26 free
27 circumferential surface
28 opening of aneurysm
30 free
32 free
34 webs
36 cell
40 embolisation means
42 coil wire
44 delivery means
46 liquid embolic
48 free
50 free
52 pore
54 further pores
56 X-ray marker
L length

What is claimed is:

1. A medical kit for treatment of a vascular malformation comprising:

a permanently implantable covering device covering the vascular malformation, wherein the covering device has a tubular self-expandable mesh structure and a covering produced from an electrospun fabric, wherein the covering is connected to the mesh structure and at least partially covers the mesh structure in order to be placed over the vascular malformation in an implanted state; and an embolisation means which, in the implanted state, is configured for transport by a delivery means for the treatment of the vascular malformation, wherein the covering forms a porous membrane adapted to be penetrated by the delivery means for application of the embolisation means and is adapted to lie against an outer circumference of the delivery means when in a penetrated state, wherein the porous membrane of the covering is adapted to at least partially contract an opening formed by the delivery means when the porous membrane is penetrated following removal of the delivery means, wherein the porous membrane of the covering is adapted to contract the opening by at most 80% of a diameter of the delivery means, wherein the delivery means has a distal outer diameter of at most 0.7 mm, and wherein in an expanded state, cells of the mesh structure have an inscribed diameter or are expanded to the inscribed diameter which corresponds to at least an external diameter of the delivery means.

2. The medical kit according to claim 1, wherein the covering is porous in a manner such that in the implanted state, the covering retains the applied embolisation means.

3. The medical kit according to claim 2, wherein the covering has a porosity of greater than 0% to at most 70%.

4. The medical kit according to claim 2, wherein the covering has a porosity from 5% to 70%.

5. The medical kit according to claim 1, wherein the covering extends over at most 70% of a circumference of the mesh structure.

6. The medical kit according to claim 1, wherein the covering extends over an entire circumference of the mesh structure.

7. The medical kit according to claim 1, wherein the covering has at least 10 pores with a size of at least 15 $\mu m^2$ to less than 10000 $\mu m^2$ over an area of 100000 $\mu m^2$.

8. The medical kit according to claim 1, wherein the mesh structure is formed from webs connected together in one piece and delimited in closed diamond-shaped cells.

9. The medical kit according to claim 1, wherein the expandable mesh structure includes a braid formed from one or more wires that are movable relative to each other at points of intersection.

10. The medical kit according to claim 1, wherein the embolisation means comprises at least one deformable wire.

11. A medical kit for treatment of a vascular malformation comprising:

a permanently implantable covering device covering the vascular malformation, wherein the covering device has a tubular self-expandable mesh structure and a covering produced from an electrospun fabric, wherein the covering is connected to the mesh structure and at least partially covers the mesh structure in order to be placed over the vascular malformation in an implanted state, wherein the covering includes an electrospun fabric having pores formed by electrospinning, wherein the fabric is perforated, at least in regions, by further pores formed by laser cutting or thermal widening using a laser; and an embolisation means which, in the implanted state, is configured to be applied by means of a delivery means for the treatment of the vascular malformation, wherein the covering forms a porous membrane adapted to be penetrated by the delivery means for application of the embolisation means and is adapted to lie against an outer circumference of the delivery means when in a penetrated state, wherein the porous membrane of the covering is adapted to at least partially contract an opening formed by the delivery means when the porous membrane is penetrated following removal of the delivery means, wherein the porous membrane of the covering is adapted to contract the opening by at most 80% of a diameter of the delivery means, wherein the delivery means has a distal outer diameter of at most 0.7 mm, and wherein in an expanded state, cells of the mesh structure have an inscribed diameter or are expanded to the inscribed diameter which corresponds to at least the external diameter of the delivery means.

12. The medical kit according to claim 11, wherein the pores cover at least 25% of the circumference of the expandable mesh structure.

13. The medical kit according to claim 11, wherein the further pores are formed in both axial directions outwards from an axial centre of the expandable mesh structure.

14. The medical kit according to claim 11, wherein a size of the further pores is at least 50 μm.

15. The medical kit according to claim 11, wherein separations of the further pores with respect to each other in regards to a diameter of the further pores is at least one times distance.

16. The medical kit according to claim 11, wherein a circumferential contour of the covering is marked by a radiopaque means, at least in sections.

17. The medical kit according to claim 11, wherein the fabric has a radiopaque means.

18. A permanently implantable stent for treatment of a vascular malformation comprising:

a covering device having a tubular self-expandable mesh structure and a covering produced from an electrospun fabric, wherein the covering is connected to the mesh structure and at least partially covers the mesh structure in order to be placed over the vascular malformation in an implanted state, wherein the covering forms a porous membrane adapted to be penetrated by a delivery means for application of an embolisation means and is adapted to lie against an outer circumference of the delivery means when in a penetrated state, wherein the porous membrane of the covering is adapted such that an opening formed by the delivery means upon penetration of the membrane contracts by at most 80% of a diameter of the delivery means after removal of the delivery means, wherein the delivery means has a distal outer diameter of at most 0.7 mm, and wherein the covering comprises at least 10 pores which have a size of at least 15 $\mu m^2$ over an area of 100000 $\mu m^2$, wherein in an expanded state, cells of the mesh structure have the inscribed diameter or is expanded to an inscribed diameter which corresponds to at least the external diameter of the delivery means.

* * * * *